United States Patent
Haffner et al.

(10) Patent No.: US 6,533,764 B1
(45) Date of Patent: Mar. 18, 2003

(54) TWIST HOUSING APPARATUS FOR INSTILLING A MEDICATION INTO AN EYE

(75) Inventors: David S. Haffner, Mission Viejo, CA (US); Patrick A. Myall, San Francisco, CA (US); Bill Evans, San Francisco, CA (US)

(73) Assignee: Allergan, Inc., Irvine, CA (US)

( * ) Notice: Subject to any disclaimer, the term of this patent is extended or adjusted under 35 U.S.C. 154(b) by 199 days.

(21) Appl. No.: 09/707,006

(22) Filed: Nov. 6, 2000

(51) Int. Cl.$^7$ ............................................. A61M 35/00
(52) U.S. Cl. ........................ 604/298; 604/294; 604/289; 604/108; 222/167
(58) Field of Search ................................. 604/294–302, 604/108, 109, 157, 211, 165.04; 222/321.8, 167

(56) References Cited

U.S. PATENT DOCUMENTS

| | | | |
|---|---|---|---|
| 4,792,334 A | 12/1988 | Py | 604/301 |
| 4,946,452 A | 8/1990 | Py | 604/301 |
| 4,981,479 A | 1/1991 | Py | 604/302 |
| 5,085,651 A | 2/1992 | Py | 604/298 |
| 5,133,702 A | 7/1992 | Py | 604/302 |
| 5,163,929 A | 11/1992 | Py | 604/298 |
| 5,267,986 A | 12/1992 | Py | 604/294 |
| 5,320,845 A | 6/1994 | Py | 424/427 |
| 5,401,259 A | 3/1995 | Py | 604/294 |
| 5,499,751 A | 3/1996 | Meyer | 222/386 |
| D368,774 S | 4/1996 | Py | D24/113 |
| D374,719 S | 10/1996 | Py | D24/120 |
| 5,613,957 A | 3/1997 | Py | 604/294 |
| 5,641,004 A | 6/1997 | Py | 141/3 |
| 5,685,869 A | 11/1997 | Py | 604/294 |
| 5,746,728 A | 5/1998 | Py | 604/298 |
| 5,855,322 A | 1/1999 | Py | 239/11 |
| 4,908,024 A | 3/1999 | Py | 604/300 |

*Primary Examiner*—Dennis Ruhl
*Assistant Examiner*—Linh Truong
(74) *Attorney, Agent, or Firm*—Walter A. Hackler

(57) ABSTRACT

Apparatus for instilling a medicament into an eye includes a housing having a longitudinal axis and a chamber disposed in the housing for containing a medicament. A nozzle is provided for instilling a dose of medicament into an eye and an actuator meters doses of medicament from the chamber to the nozzle and forces each metered dose through the nozzle upon axial displacement of the actuator along housing longitudinal axis. A spring causes the axial displacement of the actuator upon release of the spring from a compressed state. A collar disposed for rotation about the housing longitudinal axis is provided by compressing the spring by twisting the collar about the housing longitudinal axis and a trigger disposed in a housing is provided for releasing the compressed spring.

21 Claims, 4 Drawing Sheets

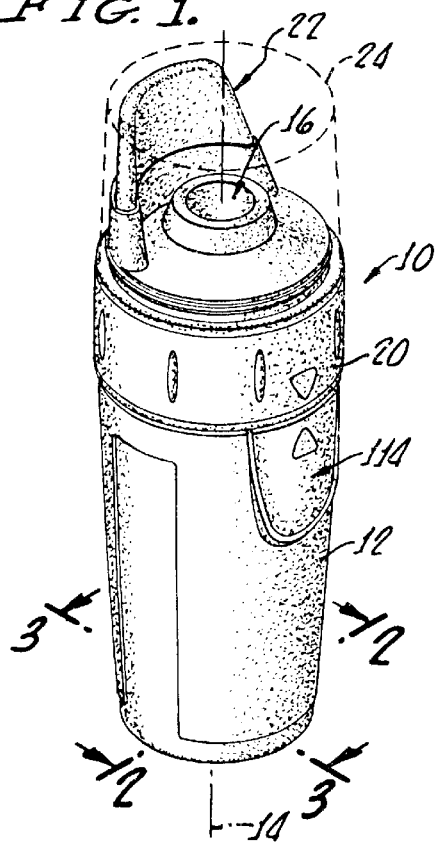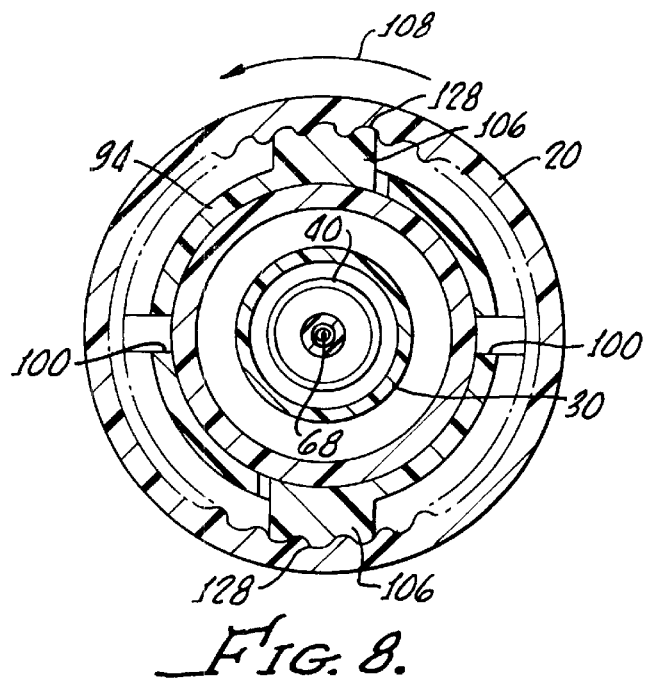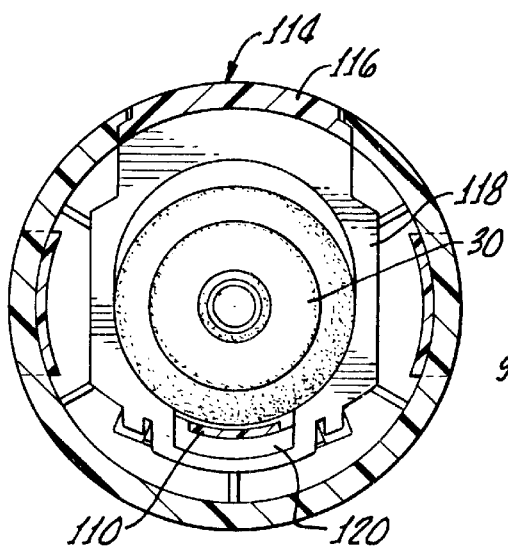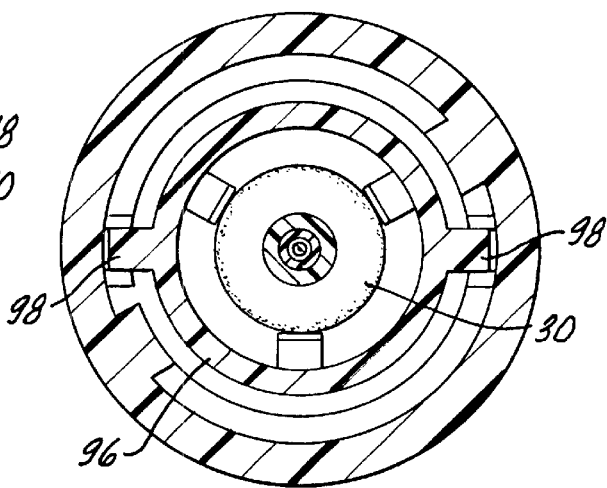

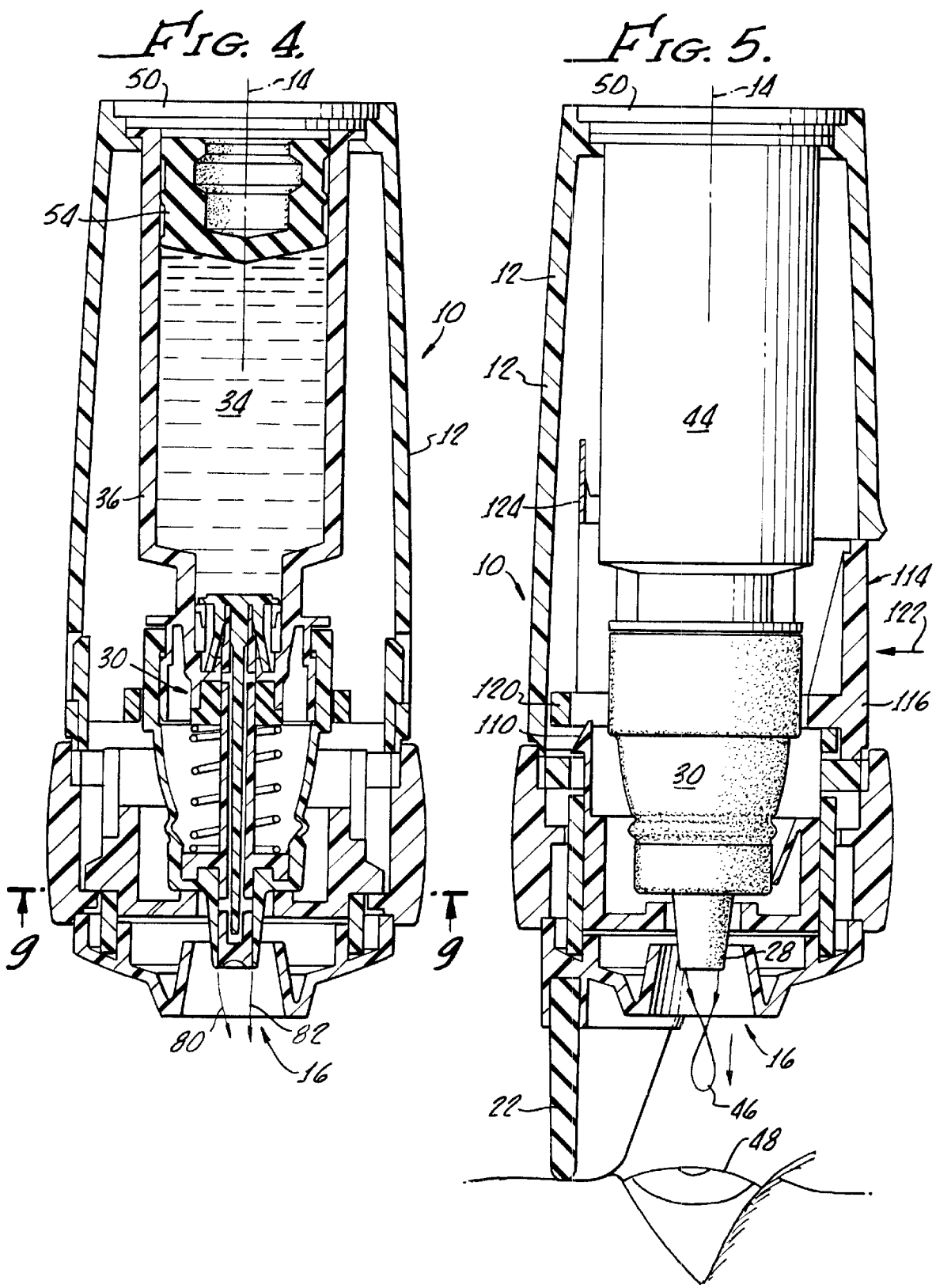

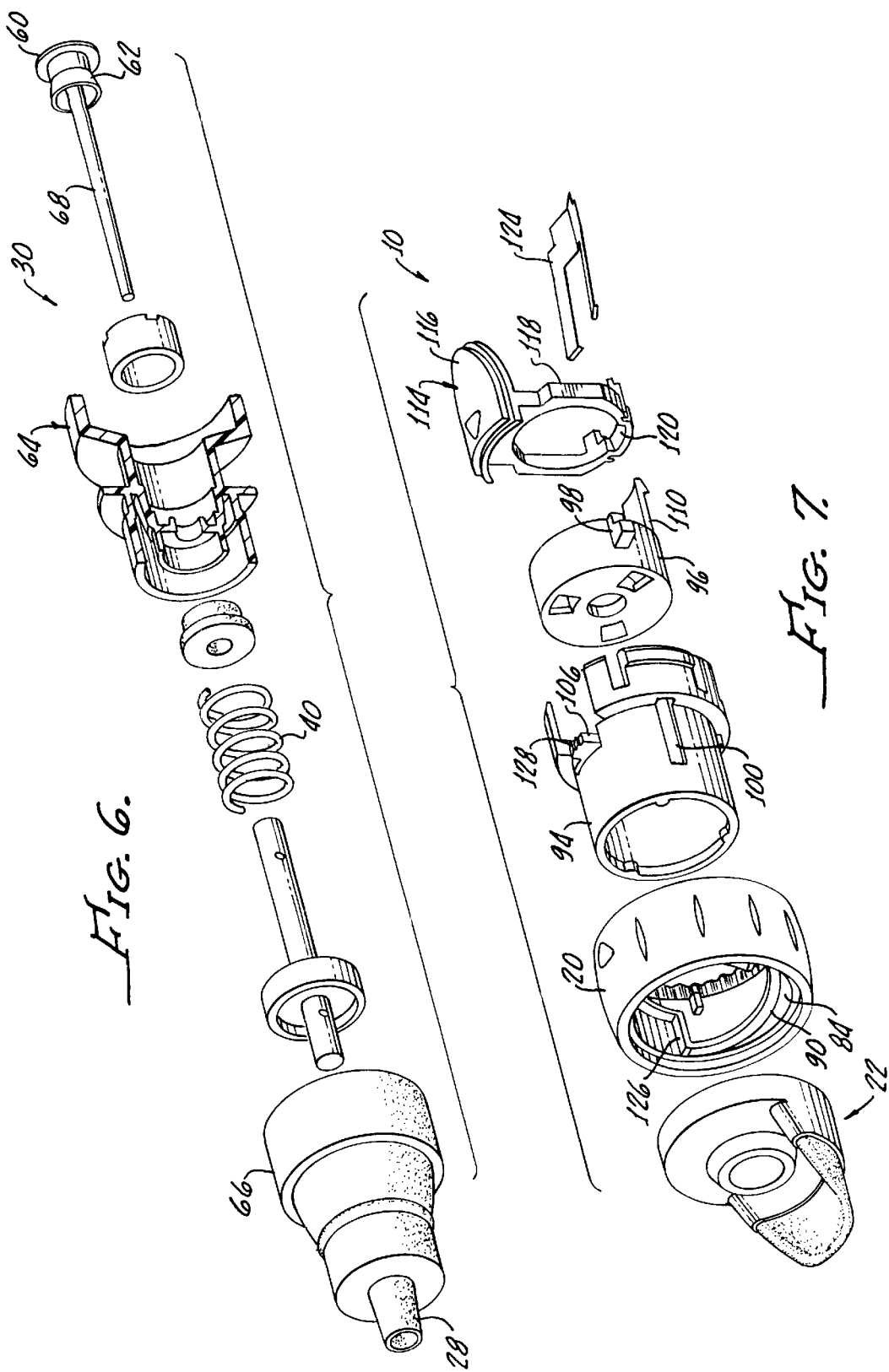

TWIST HOUSING APPARATUS FOR INSTILLING A MEDICATION INTO AN EYE

FIELD OF THE INVENTION

The present invention generally relates to apparatus for dispensing micro liter amounts of medicament and is more particularly directed to apparatus for instilling a medicament into an eye.

BACKGROUND OF THE INVENTION

A great number of devices have been developed for instilling medicament to an eye. Well known eye drop containers conventionally include a squeezable container and a nozzle for releasing drops of medicament into the eye by compression of the container. Obviously, this apparatus affords no practical method of dispensing a measured dose of medicament inasmuch as the liquid dispensed from the nozzle is dependent upon the amount of compression of the container. Thus, there is no way of accurately controlling the volume of each dose of medicament released into the eye and, further, the smallest drop obtainable is the result of the combined effective gravity and surface tension.

When preservative-free medicaments are utilized, simple eye drop dispensers are not practical because there are no means for preventing the tip from being contaminated due to its exposure to air. Such tip contamination ultimately spreads to the medicament in the container.

In an attempt to overcome these problems, apparatus has been developed for applying a medicament to an eye which includes a nozzle having a seam which is normally in a closed position for preventing the passage of medicament through the nozzle, and which opens in response to a flow of medicament of sufficient pressure to enable opening of the seam in order to permit the passage of medicament through the nozzle for release into the eye, see U.S. Pat. No. 5,685,869.

While this nozzle is suitable, there is difficulty in coupling the nozzle with a suitable reservoir of medicament in order to create a working, producible device for multiple dose delivery of a preservative-free product of sufficient dose accuracy for consumer benefit and regulatory body registration over an extended period of time of up to six months or more.

Operation of prior art devices such as set forth in the hereinabove referenced U.S. patent typically causes a small negative pressure or vacuum within the medicament container during operation. When a collapsible container is utilized to accommodate shrinking of volume of the medicament reservoir, the materials of construction do not satisfactorily inhibit the permeating of air through the container walls to provide a desired long term use in storage of the device without compromise of the stored medicament.

U.S. patent application Ser. No. 09/435,703 filed Nov. 8, 1999 entitled MULTIPLE PRECISION DOSE PRESERVATIVE FREE MEDICATION DELIVERY SYSTEM provides a nozzle and medicament reservoir combination which enables multiple dose delivery of a preservative-free product with accurate dose dispensing over extended periods of time.

The delivery system disclosed in the hereinabove referenced Ser. No. 09/435,703 required axial movement in order to compress a spring for operation thereof. No mechanical advantage is provided and the force required may be objectionably excessive which could cause user dissatisfaction with the delivery system.

The present invention provides for apparatus enabling the axial compression of a spring by rotation of a collar, handle, knob or ring. Further, the apparatus in accordance with the present invention provides a mechanical advantage though the use of an incline in order to reduce the force required of the patient for utilizing the system.

SUMMARY OF THE INVENTION

Apparatus in accordance with the present invention for operating an eye drop dispenser, including a chamber for containing a medicament, a nozzle for instilling a dose of medicament into an eye and a spring driven actuator for metering doses of medicament from the chamber to the nozzle, generally includes a housing for removably receiving the chamber and a collar disposed for rotation about the housing for compressing the actuator spring by twisting said collar about the housing. A trigger disposed in the housing is provided for releasing the compress spring.

More particularly, the collar includes a ring with an internal cam surface and the apparatus further comprising a mandrel for supporting the collar and ring for rotation thereabout. A slider is disposed within the mandrel and includes a traveler for engaging a cam surface through a slot in the mandrel. Rotation of the collar causes longitudinal movement of the traveler and slider for compressing the spring.

In addition, the ring may include an internal gear tooth surface and the mandrel may include a ratchet for engaging the tooth which enables rotation of the collar and ring only in a direction for compressing the spring.

More particularly, the slider includes a hook latch for holding the slider in a position compressing the spring and the trigger includes a push button and a depending member having a strikeplate for engaging a hook latch.

In addition, the trigger may further include a leaf spring for engaging the strikeplate into a position for engaging the hook latch, the switch plate being moved out of engagement with the hook latch upon depression of the push button.

In combination, the present invention provides apparatus for instilling a medicament into an eye which includes a housing having a longitudinal axis and a chamber disposed in the housing for containing a medicament. A nozzle is provided for instilling a dose of medicament into an eye and an actuator for metering doses of medicament from the chamber to the nozzle and forcing the metered doses through the nozzle upon axial displacement of the actuator along the housing longitudinal axis.

A spring is provided for causing the lateral displacement of the actuator upon release of the spring from a compressed state.

A collar, disposed for rotation about the housing longitudinal axis, is provided for compressing the spring by twisting the collar about the housing longitudinal axis and a trigger disposed in the housing is provided for releasing the depressed spring.

In this combination, the collar includes a ring with an internal cam surface and the apparatus further comprises a mandrel for supporting the collar and ring for rotation thereabout along with a slider disposed within the mandrel having a traveler for engaging the cam surface through a slot in the mandrel. Rotation of the collar and ring causes longitudinal movement of the traveler and slider for compressing the spring.

The ring may include an internal tooth surface and the mandrel may include a ratchet for engaging the gear tooth surface for enabling rotation of the collar and ring only in a direction for compressing a spring.

Preferably, the slider includes a hook latch for holding slider in a position compressing a spring and a trigger includes a push botton with a depending member having a strikeplate for engaging the hook latch. Preferably the trigger includes a leaf spring for urging a strikeplate into a position for engaging a hook latch with a strikeplate being moved out of engagement with the hook latch upon depression of the push bottom in order to release the spring.

In addition, the chamber and nozzle and actuator may be removed as a single unit, thus enabling replenishment of medicament.

BRIEF DESCRIPTION OF THE DRAWINGS

The advantages and features of the present invention will be better understood by the following description when considered in conjunction with the accompanying drawings in which:

FIG. 1 is a perspective view of apparatus in accordance with the present invention generally showing a housing, a collar, as hereinafter described for compressing an axial spring, and a trigger for releasing the spring;

FIG. 4 is a cross-sectional view similar to FIG. 2 showing the spring being released and forcing a metered dose of medicament from the nozzle;

FIG. 5 is a partial cross-sectional view similar to FIG. 3.

FIG. 6 is an exploded perspective view more clearing showing the nozzle and actuator;

FIG. 7 is an exploded perspective view more clearly showing the collar having a ring therein along with a mandrel slider and trigger mechanism for controlling compression and release of the spring;

FIG. 8 is an cross-sectional view taken along the line 8—8 of FIG. 2 indicating the rotation of the collar and ring for compressing a spring;

FIG. 9 is a cross-sectional view taken along the line 9—9 of FIG. 4; and

FIG. 10 is a cross-sectional view taken along line 10—10 of FIG. 2.

DETAILED DESCRIPTION

Figure 2:
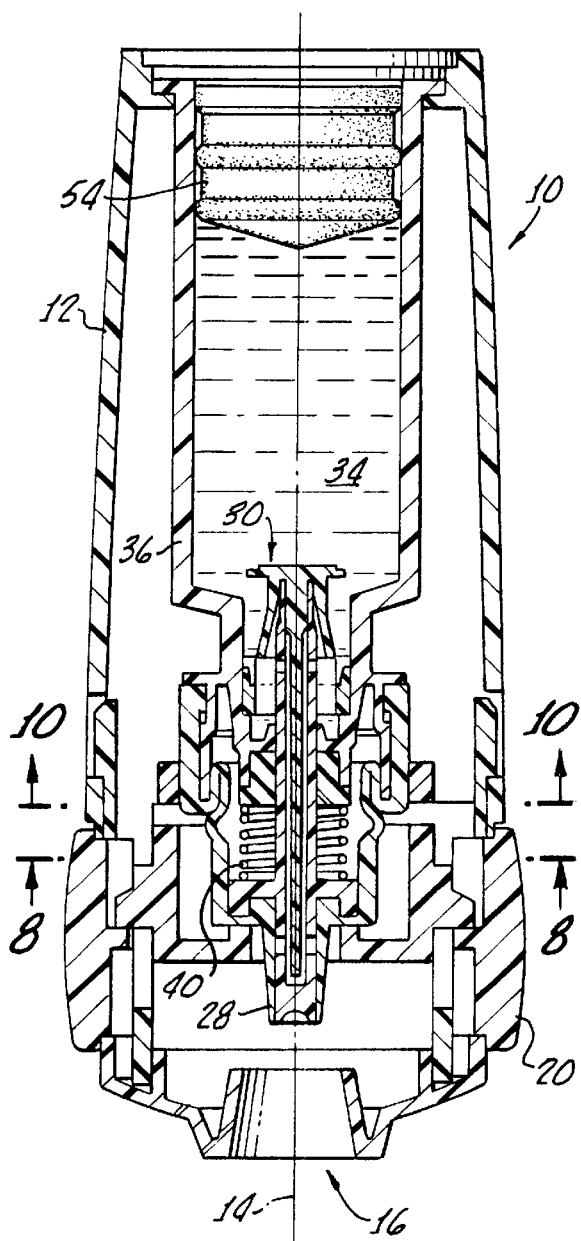
FIG. 2 is a cross-sectional view of the apparatus showing FIG. 1 along line 2—2 and more clearly showing a chamber disposed within the housing, a nozzle for instilling a dose of medicament into an eye and an actuator for metering doses of medicament from the chamber to the nozzle along with an axial spring in a compressed state.

With reference to FIG. 1, there is illustrated in apparatus 10 in accordance with the present invention for instilling a medicament (not shown) into an eye (not shown). Shown in FIG. 1 are a housing 12 having a longitudinal axis 14, a nozzle 16, for instilling a dose of medicament to the eye and a collar 20 which provides a rotatable means accessible from an exterior of the housing 12 for compressing a spring as will be hereinafter described in greater detail.

An eye piece 22 is provided for stabilizing the apparatus 10 in position for instilling a medicament into a user's eye and a cap 24, shown in dashed line, is utilized to cover the nozzle 16 and eye piece 22 when the apparatus 10 is not in use.

Figure 3:
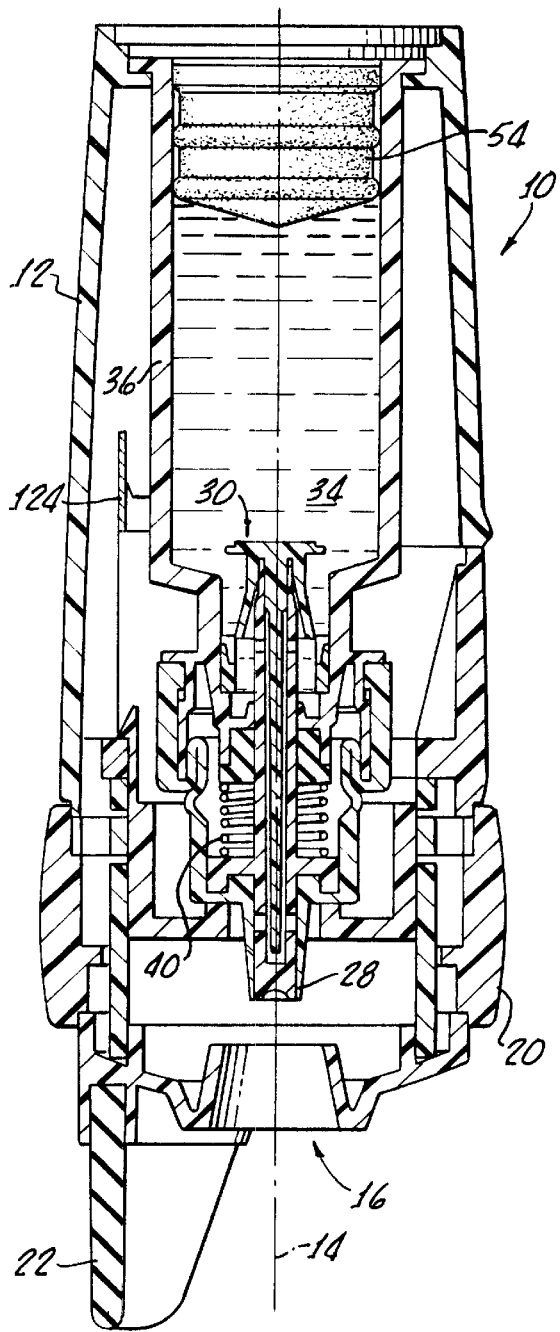
FIG. 3 is a cross-sectional of a view similar to that of FIG. 2 taken along the line 3—3 of FIG. 1.

With reference to FIGS. 2 and 3, there is shown cross-sections of the apparatus 10 showing more clearly, as part of the nozzle 16, a nozzle tip 28 and an actuator 30 for metering doses of a medicament 34 from a chamber 36 disposed in the housing 12. The actuator 30 upon axial or longitudinal motion meters doses of medicament to the nozzle tip 28 and forcing each metered dose throughout the nozzle tip 28 and nozzle 16 upon axial displacement of the actuator along the housing longitudinal axis 14. The actuator and chamber is fully described in U.S. patent application Ser. No. 09/435,703 hereinabove referenced, and is incorporated herewith in its entirety by the specific reference thereto for the purpose of describing the nozzle tip 28 actuator 30 and chamber components of the present invention.

As described in the referenced patent application, a spring 40 shown in a compressed state in FIGS. 2 and 3, causes the axial displacement of the actuator 30 upon release of the spring 40 from the compressed state as shown in FIG. 4.

FIG. 5 more clearly shows the apparatus 10 as it may be utilized with a dispenser 44 for providing metered doses 46 of medicament to an eye 48. As shown in FIG. 5, the dispenser 44 includes the chamber 36, nozzle tip 28 and actuator 30. As shown, the dispenser may be removed and replaced within the housing 12 by way of a removable end cap 50.

With reference to FIG. 6, the actuator 30, described as a reciprocating pump U.S. patent application Ser. No. 09/435,703, seals the chamber 36 and is in fluid communication with the medicament 34. A stopper 54 slidably disposed within the chamber 36, accommodates for long term pressure differentials by gradually decreasing the chamber housing as medicament is metered therefrom.

The actuator 30 includes a pump head 60 with an annular skirt valve 62 disposed within a pump body 64. The actuator 30 is assembled and attached to the chamber by a collapsible boot 66.

FIGS. 2 and 3 show the actuator 30 in a "cocked" position with a compressed spring 40 and the skirt valve 62 in a set back position in which forward movement upon released from the "cocked position" traps a dose of medicament and removes same from chamber 36 and out of the nozzle 16 as indicated by the arrows 80, 82 in FIG. 4. All of this apparatus is more clearly defined in the incorporated U.S. patent application Ser. No. 09/435,703.

With reference to FIG. 7, rotatable means accessible from exterior of the housing 12 for compressing the spring 40 is represented by collar 20. More practically, the collar 20 includes a ring 88 with an internal cam surface 90. A mandrel 94 is provided for supporting the collar 20 and ring 88 for rotation thereabout. A slider 96 sized for disposition within the mandrel 94, includes two travelers 98 for engaging the cam surface 90 through two slots 100 in the mandrel 94.

In operation, twisting or rotation of the collar 20 and ring 88 around the mandrel 94, causes the traveler 98 and slider 96 to move in a longitudinal or axial direction due to the engagement of the slider 98 with a cam surface 90. Rearward motion of the slider 96 compresses the spring 40 and effectively "cocks" the actuator 30 as also shown in FIG. 8. The ring 88 includes an internal gear tooth surface 104 and the mandrel 94 includes a ratchet 106 for engaging the gear tooth surface 104 and enabling rotation of the collar 20 and ring 88 only in a direction for compressing the spring as indicated by the arrow 108 in FIG. 8.

The cam surface 90 and traveler 98 provides for a slider 98 mechanism for cocking the spring 40 by easy twisting of the collar 20. A mechanical advantage afforded by the cam surface 90 and the traveler 98 enables compression of the spring 40 with minimal torque requirement on a patient. FIG. 9 is a cross-sectional view more clearly showing the engagement between the cam surface 90 and the traveler 98.

With further reference to FIG. 7, the slider 96 includes a hook latch 110 for holding the slider at 96 in a position compressing the spring 40 as shown in FIGS. 2,3 and 10. A trigger 114 disposed in the housing 12 is provided for releasing the compressed spring 40. More particularly, the trigger 114 includes a push button 116 and a depending member 118 having a strikeplate 120 for engaging a hook latch 110.

Depression of the trigger 114 by the push botton 116 as indicated by the arrow 122 in FIG. 5, causes the strikeplate 120 to be removed from engagement from the hook latch 110, thereby releasing the spring 40 and enabling the actuator 30 to move in an axial or Longitudinal direction for metering a dose of medicament 34 through the nozzle 16 as indicated by the drop 46 in FIG. 5.

To ensure engagement of the strikeplate 120 and hook latch 110 when the push button 116 is not depressed, a leaf spring 124 is provided for urging the strikeplate 120 into a position for engaging the hook latch 110.

In operation at the completion of rotation of the collar 20 and ring 88, the traveler 98 falls off an end 126 of the cam surface 90. Subsequent release of the trigger 114 by depression of the push button 116 allows the dispensing of medicament as hereinabove described. The slider 96 and traveler 98 are then positioned once again for the next dosing cycle by another rotation of the collar 20 and ring 88.

The collar 20 and ring 88 are configured for compressing a spring with 1800 rotation. Once this full rotation is reached the actuator 30 is fully cocked with the spring 40 compressed and the hook latch 110 engages a strikeplate 120. Prior to reaching the 180° point, the geared surface 104 and ratchet 106 provides an anti-rotation mechanism which prevents the slider from moving if the collar 20 is released by a user. Accordingly, if a 180 ° rotation is difficult for a user because of a condition such as arthritis or some other aliment of the hand or the rest, the user can achieve the 180 ° rotation in two or more twisting efforts after re-griping the collar.

In addition, the ratchet 106 prevents the rotation of collar 20 and ring 88 in a wrong direction. However, since the mechanism is fabricated from molded plastic parts, the mechanism has sufficient but limited strength to resist rotation in a wrong direction. If sufficient torque is applied to the collar in a direction opposite that of cocking the actuator 30, the surface 104 breaks free from the ratchet 106 and allows rotation in the opposite direction rather than causing permanent damage to the geared surface 104 and ratchet 106. This is achieved by the shape of the ratchet teeth 126 and clearances between the ratchet teeth 126 and the geared surface 104.

Although there has been hereinabove described apparatus for instilling a medicament into an eye in accordance with the present invention for the purpose of illustrating the manner in which the invention may be used to advantage, it will be appreciated that the invention is not limited thereto. Accordingly, any and all modifications, variations or equivalent arrangements which may occur to those skilled in the art, should be considered to be within the scope of the inventions as defined in the appended claims.

What is claimed is:

1. Apparatus for instilling a medicament into an eye, said apparatus comprising:
    a housing having a longitudinal axis;
    a chamber disposed in said housing for containing a medicament;
    a nozzle for instilling a dose of the medicament into an eye;
    an actuator for metering doses of medicament from said chamber to said nozzle and forcing each metered dose through said nozzle upon axial displacement of said actuator along the housing longitudinal axis;
    a spring for causing said axial displacement of said actuator upon release of said spring from a compressed state;
    a collar disposed for rotation about the housing longitudinal axis for compressing said spring by twisting said collar about the housing longitudinal axis; and
    a trigger disposed in said housing for releasing the compressed spring.

2. The apparatus according to claim 1 wherein said collar includes:
    a ring with an internal cam surface and the apparatus further comprises a mandrel for supporting the collar and ring for rotation thereabout and a slider disposed within said mandrel having a traveler for engaging the cam surface through a slot in said mandrel, rotation of said collar and ring causing longitudinal movement of the traveler and slider for compressing said spring.

3. The apparatus according to claim 2 wherein said ring includes an internal gear tooth surface and said mandrel includes a ratchet for engaging the gear tooth surface and enabling rotation of the collar and ring only in a direction for compressing said spring.

4. The apparatus according to claim 3 wherein said slider includes a hook latch for holding the slider in a position compressing said spring.

5. The apparatus according to claim 4 wherein said trigger includes a push button and a depending member having a strikeplate for engaging said hook latch.

6. The apparatus according to claim 5 wherein said trigger further includes a leaf spring for urging said strikeplate into a position for engaging said hook latch, said strikeplate being moved out of engagement with said hook latch upon depression of said pushbutton.

7. The apparatus according to claim 6 wherein said chamber, nozzle and actuator are removable as a single unit from said housing.

8. Apparatus for operating an eye drop dispenser, said eye drop dispenser including a chamber for containing a medicament, a nozzle for instilling a dose of the medicament into an eye and a spring driven actuator for metering doses of medicament from said chamber to said nozzle and forcing each metered dose through said nozzle upon axial displacement of said actuator along a chamber longitudinal axis; said apparatus comprising:
    a housing for removably receiving said chamber, nozzle and actuator;
    a collar disposed for rotation about the housing for compressing the actuator spring by twisting said collar about the housing; and
    a trigger disposed in said housing for releasing the compressed spring.

9. The apparatus according to claim 8 wherein said collar, includes:
    a ring with an internal cam surface and the apparatus further comprises a mandrel for supporting the collar and ring for relation thereabout and a slider disposed within said mandrel having a traveler for engaging the cam surface through a slot in said mandrel, rotation of said collar and ring causing longitudinal movement of the traveler and slider for compressing said spring.

10. The apparatus according to claim 9 wherein said ring includes an internal gear tooth surface and said mandrel includes a ratchet for engaging the gear tooth surface and enabling rotation of the collar and ring only in a direction for compressing said spring.

11. The apparatus according to claim 10 wherein said slider includes a hook latch for holding the slider in a position compressing said spring.

12. The apparatus according to claim 11 wherein said trigger includes a pushbutton and a depending member having a strikeplate for engaging said hook latch.

13. The apparatus according to claim 12 wherein said trigger further includes a leaf spring for urging said strikeplate into a position for engaging said hook latch, said strikeplate being moved out of engagement with said hook latch upon depression of said pushbutton.

14. Apparatus for instilling a medicament into an eye, said apparatus comprising:

a housing having a longitudinal axis;

a chamber disposed in said housing for containing a medicament;

a nozzle for instilling a dose of the medicament into an eye;

an actuator for metering doses of medicament from said chamber to said nozzle and forcing each metered dose through said nozzle upon axial displacement of said actuator along the housing longitudinal axis;

a spring for causing said axial displacement of said actuator upon release of said spring from a compressed state;

rotatable means accessible from an exterior of said housing for compressing said spring; and a trigger disposed in said housing for releasing the compressed spring.

15. The apparatus according to claim 14 wherein said rotatable means comprises a collar.

16. The apparatus according to claim 15 wherein said collar includes a ring with an internal cam surface and the apparatus further comprises a mandrel for supporting the collar for rotation thereabout and a slider disposed therein, said mandrel having a traveler for engaging the cam surface thereon a slot in said mandrel; rotation of said collar causing longitudinal movement of the traveler and slider for compressing said spring.

17. The apparatus according to claim 16 wherein said ring includes an internal gear tooth surface and said mandrel includes a ratchet for engaging the gear tooth surface and enabling rotation of the collar and ring only in a direction for compressing said spring.

18. The apparatus according to claim 17 wherein said slider includes a hook latch for holding the slider in a position compressing said spring.

19. The apparatus according to claim 18 wherein said trigger includes a pushbutton and an depending member having a strikeplate for engaging said hook latch.

20. The apparatus according to claim 19 wherein said trigger further includes a leaf spring for urging said strikeplate into a position for engaging said hook latch, said strikeplate being moved out of engagement with said hook latch upon depression of said pushbutton.

21. The apparatus according to claim 20 wherein said chamber nozzle and actuator are removable as a single unit from said housing.

* * * * *